(12) United States Patent
Casey et al.

(10) Patent No.: US 6,636,760 B1
(45) Date of Patent: Oct. 21, 2003

(54) PLANAR TRANSDUCER FOR MEASURING BIOMEDICAL PRESSURES

(76) Inventors: Vincent Casey, Foxgrove House, Rockbarton, Bruff (IE); Stephen O'Sullivan, Nemo, Roxboro Road, Limerick (IE); Ronan Nagle, Vandeleur Street, Kilrush (IE)

(*) Notice: Subject to any disclaimer, the term of this patent is extended or adjusted under 35 U.S.C. 154(b) by 0 days.

(21) Appl. No.: 09/719,211
(22) PCT Filed: Jul. 3, 1998
(86) PCT No.: PCT/IE98/00056
§ 371 (c)(1), (2), (4) Date: Feb. 23, 2001
(87) PCT Pub. No.: WO00/01296
PCT Pub. Date: Jan. 13, 2000

(51) Int. Cl.[7] ................................ A61B 6/00
(52) U.S. Cl. .................... 600/480; 600/561; 73/705
(58) Field of Search .............. 600/561, 480, 600/485; 73/705

(56) References Cited

U.S. PATENT DOCUMENTS

| | | | | |
|---|---|---|---|---|
| 3,789,667 A | * | 2/1974 | Porter et al. .................. | 73/705 |
| 3,875,481 A | | 4/1975 | Miller et al. | |
| 4,266,263 A | | 5/1981 | Haberl et al. | |
| 4,526,043 A | | 7/1985 | Boie et al. | |
| 4,611,600 A | * | 9/1986 | Cohen ........................ | 600/480 |
| 4,869,265 A | | 9/1989 | McEwen | |
| 5,107,846 A | * | 4/1992 | Atlas ..................... | 250/227.21 |
| 5,195,375 A | | 3/1993 | Tenerz et al. | |
| 5,284,150 A | * | 2/1994 | Butterfield et al. ......... | 600/485 |
| 5,313,957 A | * | 5/1994 | Little ........................ | 600/480 |
| 5,425,371 A | * | 6/1995 | Mischenko ................ | 600/480 |
| 5,693,886 A | | 12/1997 | Seimiya et al. | |

FOREIGN PATENT DOCUMENTS

| | | | |
|---|---|---|---|
| EP | 0 348 224 A | * | 12/1989 |
| WO | WO 90 07906 A | * | 7/1990 |
| WO | WO 97 49332 A | * | 12/1998 |

OTHER PUBLICATIONS

International Search Report From EPO on the Corresponding International Application, PCT/IE98/00056.*
International Preliminary Examination Report From EPO for PCT/IE98/00056.*
Neuman et al; Capacitive Sensors for Measuring Finger and Thumb Tip Forces; IEEE Front. of Eng and Comp in Health Care; Jan. 1984; pp436–439.
Lotters et al; Polydimethylsiloxane as an elastice material applied in a capacitive accelerometer; J. Micro Machn'g; Jan. 1996; pp 52–54.
Beebe et al; A Silicon–Based Tactile Sensor for Finger–Mounted Applications; IEEE Trans. on Biomedical Eng'g; Vol 45 Feb. 1998; pp 151–158.
Golby; et al; The development of fibre–optic disposable pressure transducer for medical applications; SPIE vol. 1011 Fib Optic Sensors III; Jan. 1998; pp 136–143.
Jones et al; Intensity and Wavelength–Based Sensors and Optical Actuators; Opt. Fiber Sens: Systems and Applications; VII Artech House; circa 1/98 pp 431–445.
Muraza et al; Schemes for referencing of intensity–modulated optical sensor systems; Optical Fiber Sensor Technology; Jan. 1995; Chapman and Hall, Ldn; pp 383–407.

* cited by examiner

*Primary Examiner*—Michael Powell Buiz
*Assistant Examiner*—Ramesh Krishnamurthy
(74) *Attorney, Agent, or Firm*—Ipsolon LLP

(57) ABSTRACT

A planar pressure transducer is disclosed which is useful for interposing between living tissue and a medical device that applies pressure to the tissue in order to estimate the pressure applied to a selected area of the tissue. The planar pressure transducer comprises a pair of opposed plates between which the proximal ends of optical fibers and a deformable polymer structure are disposed. When the plates are subjected to a pressure acting normally to the plane of the plates an optical signal is obtained via the distal ends of the fibers and related to the pressure acting on the plates.

18 Claims, 13 Drawing Sheets

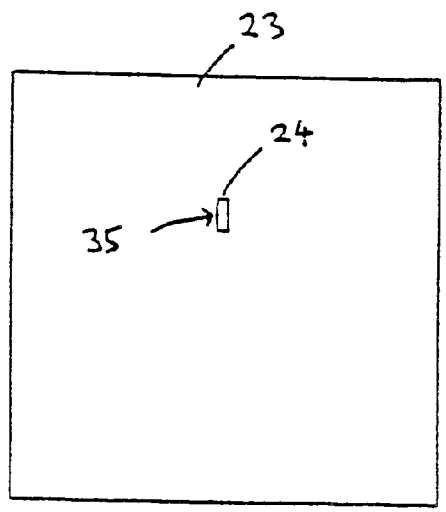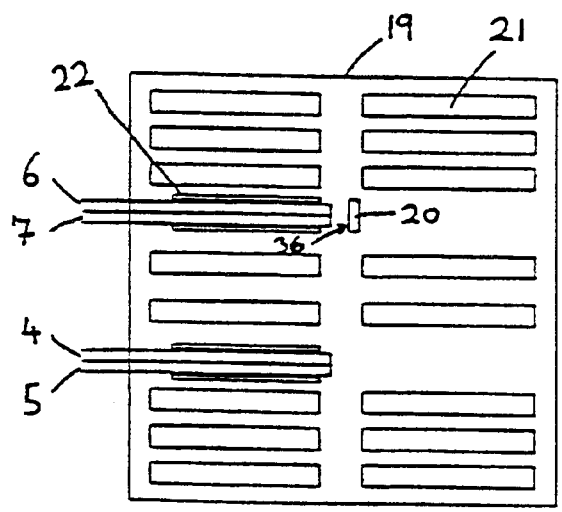
FIG. 4

PLANAR TRANSDUCER FOR MEASURING BIOMEDICAL PRESSURES

FIELD OF THE INVENTION

This invention pertains to transducers for estimating the pressure applied to body tissue by an object such as a medical device or body part. The invention particularly pertains to a new and improved transducer having at least two plates separated from one another by an elastic element formed of rubber for measuring pressures acting normal to the plates by detecting the resultant change in separation of the plates. The invention is particularly useful in health care, for interposing at the surface between a tissue and an object without substantially displacing either the tissue or the object from the surface in order to estimate the pressure applied by the object at a predetermined location.

BACKGROUND

In medical tourniquet applications it is desirable to have a transducer that establishes the actual pressure applied by a device such as a cuff to the underlying tissue, in a continuous way, as the tourniquet cuff pressure varies during a medical procedure. Such a transducer must be of low profile and small relative to the size of the cuff so that it may be interposed between the cuff and the tissue without interfering with the function of the cuff or causing tissue damage.

Force and pressure are usually sensed using the 'spring balance principle', where, in a primary transducing step, an elastic element transforms the measurand into a deflection or deformation, which, in a secondary transducing step, is converted into an electrically useful signal. Common pressure transducers tend to depend on the deformation of a spring, cantilever, or diaphragm in the primary transducing step while electrical and optical techniques are used frequently in the secondary step.

The compliance of polymer materials and rubbers, in addition to their elasticity, makes them attractive candidate materials for the primary transducing step. Weighing mats by Miller et al. in U.S. Pat. No. 3,875,481 and load cell type transducers have been developed using elastomer elements where change in capacitance is used to infer the applied pressure. Improvements in relation to hysteresis and linearity of response have resulted from the use of voids and structured elastomer elements by Haberl et al. in U.S. Pat. No. 4,266,263 and by Seimiya et al. in U.S. Pat. No. 5,693,886. However, it is difficult to realize the optimum shapes without the use of complicated cutting and assembly procedures and individual device assembly. Low profile devices incorporating elastomer elements, designed for use as tactile transducers, have also been developed as disclosed for instance by Boie et al. in U.S. Pat. No. 4,526,043. However, the noise susceptibility of capacitor based transducers in general makes them less favorable for medical applications as either large areas or sophisticated support electronics are required in order to provide a satisfactory signal-to-noise ratio.

The noise problems associated with capacitive based devices can be circumvented to a large extent through the use of optical secondary transducing techniques. Pressure transducers having a flexible, pressure deformable reflector from which light radiation is reflected, are already well known as disclosed by Tenerz et al. in U.S. Pat. No. 5,195,375. Such devices have advantages for deployment in medical catheters for in situ physiological pressure measurements. However, they require sophisticated micromachining technology to form the flexible member, which is fragile and unsuitable for direct mechanical coupling.

In a biomedical pressure transducer disclosed by McEwen in U.S. Pat No. 4,869,265, a pressurisable chamber containing integral membrane switch type electrical contacts is interposed between the tissue and an apparatus such as a tourniquet cuff. The normally closed contacts are opened when the pressure within the chamber is equal to the pressure applied by the cuff. A fluid filled line is used to translate the pressure within the chamber to a detection device which is located remotely from the tourniquet site and thereby provide an estimate of the actual pressure applied by the cuff to the tissue. This approach does not provide a continuous dynamic estimate of the pressure applied and suffers from signal damping introduced by the fluid line.

SUMMARY OF THE INVENTION

An object of the present invention is to provide a transducer which will reliably and reproducibly measure the pressure applied by any one of a number of medical devices to a portion of a human body surface, tissue or organ. A related object is that the transducer should measure the pressure, applied by a specified device at a predetermined location relative to the device, in a direction normal to the plane of the device at the predetermined location. A further related object of the present invention is that it should measure the applied pressures in the range 0–500 mmHg (10 psi) and that it should measure such pressures near the location, averaged over an area no greater than 2 $cm^2$.

A further object of the present invention is to provide a pressure transducer which is sufficiently small such that it does not introduce significant error by significantly altering the tissue/device interface during measurement A related object is that the transducer should not introduce significant error when used in measurement of pressures applied to curved surfaces in two dimensions having radii down to 2 cm.

Another object of the present invention is to provide a pressure transducer which is suitable for inclusion in a multi-transducer array. A related object is to provide a pressure transducer array which will conform to curved compliant tissue surfaces.

A further object of the present invention is to provide a transducer which does not require the use of electrical currents inside the body of the transducer. A related object is to provide a transducer which does not require the use of metal within the body of the transducer.

A further object of the present invention is to provide a transducer which permits fast, convenient calibration, or calibration checking, of the transducer in the application environment.

The present invention is provided to attain the above described objectives.

The present invention is embodied in a planar transducer for measuring biomedical pressures adapted for insertion between a tourniquet cuff and a human limb or body part to measure the pressure applied by the cuff to the limb or body part. The transducer comprises a pair of opposing plates, one a substrate plate and the other a pressure plate. It also includes a measurement channel optical fiber set with proximal end connected to the transducer and the distal end connected remotely to an electronics module. The electronics module contains the light source and photodetectors as well as support and proessing electronics. The measurement channel optical fiber set is comprised of two optical fibers, an emitter fiber, and a detector fiber for transmitting a measurement channel light beam to and from the transducer. A deformable polymer structure is located between the plates. When pressure is applied to the transducer, the deformation of the deformable polymer structure will result in a change in the degree of projection of a shutter-reflector into the measurement channel light beam. This will change the coupling of light between the emitter and detector optical fibers and thereby modulate the measurement channel light beam. A measurement photodetector located at the distal end of the measurement channel detector fiber produces an electrical signal which is representative of the intensity modulation of the measurement channel light beam. The reference channel provides an intensity reference signal. Both signals are amplified and passed to an analogue to digital (A/D) converter unit. The outputs of the A/D unit are in turn passed to a processor unit which provides an indication on the output device of the applied pressure.

BRIEF DESCRIPTION OF DRAWINGS

FIG. 4 is a plan view of the substrate and pressure plates of the preferred embodiment.

BEST MODES FOR CARRYING OUT THE INVENTION

The embodiments illustrated are not intended to be exhaustive or to limit the invention to the precise form disclosed. It is chosen and described in order to explain the principles of the invention and its application and practical use, and thereby enable others skilled in the art to utilize the invention.

Figure 1:
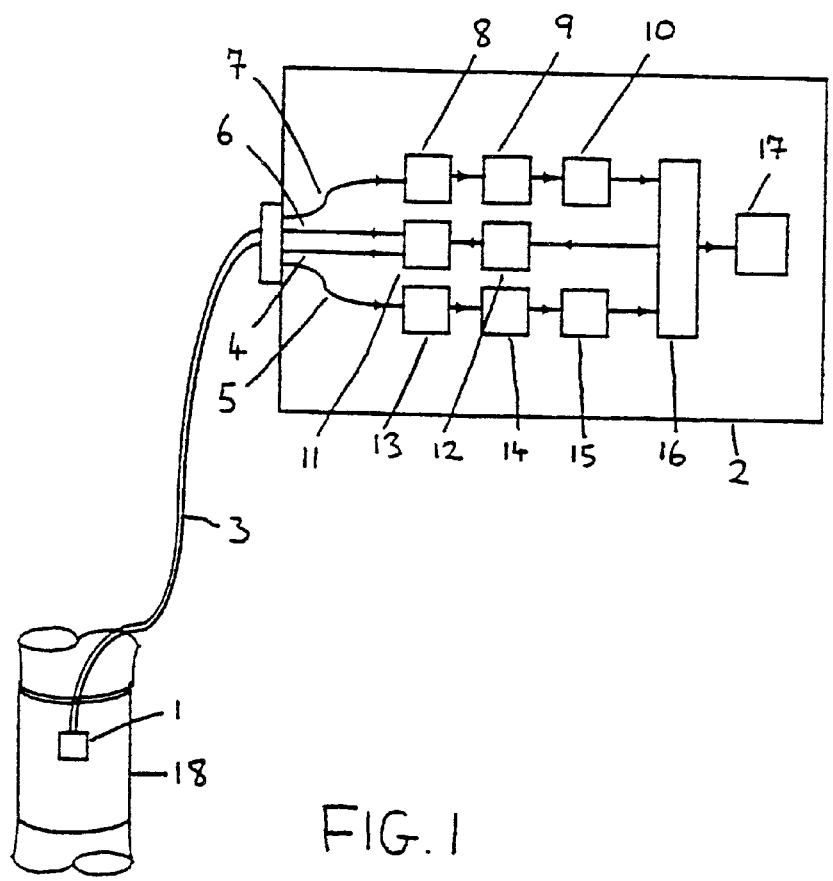
FIG. 1 is a schematic diagram depicting the pressure transducer and electronic processing circuitry of the invention.

In the preferred embodiment illustrated in FIG. 1, an LED driver circuit 12 drives the light emitting diode 11 (LED) at 1 kHz using a low duty cycle and high current to maximize the signal-to-noise ratio. The LED 11 produces optical energy having a wavelength of 850 nm. It will be apparent that some other light source such as a laser diode or incandescent lamp could be used rather than the LED to provide light for the transducer.

The pulsed light beam from the LED 11 is coupled into the emitter fibers 4, 6 of both the measurement and reference channel fiber sets. The measurement channel photodetector 8 detects the modulated intensity of the measurement channel light beam and the reference channel photodetector 13 detects the intensity of the reference light beam. The photodetectors 8, 13 produce intensity signals which are relayed along separate signal lines to identical, but separate signal processing circuits within the electronics module 2.

FIGS. 3, 4, 5, 6, 9 demonstrate the invention in greater detail. In the preferred embodiment stepped-index, multi-mode fiber is used. The various fibers of the measurement and reference channel optical fiber sets are optically coupled to the LED 11 and photodetectors 8, 13, contained within the electronics module 2, by means of a transparent optical gel potting compound 34.

Figure 2:
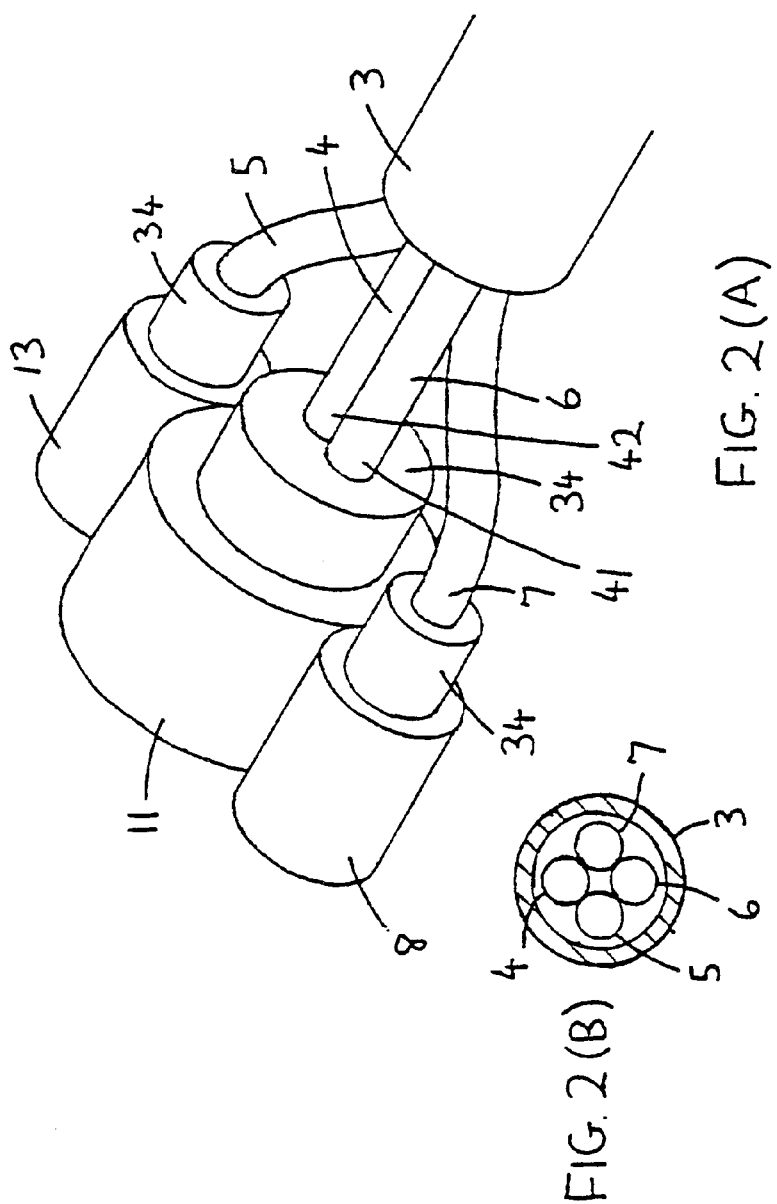
FIG. 2(A) is a pictorial representation of the distal ends of the measurement and reference channel fibers.
FIG. 2(B) is a cross-sectional view of the fibers of the measurement aid reference channels contained within a plastic tube.

In particular, each optical fiber is positioned with its distal end abutting the light emitting surface of the LED 11 or light sensitive surface of the photodetectors 8, 13 (FIG. 2(A)). The various fibers are contained within a plastic jacket 3 which links the electronics module 2 with the transducer 1. This helps ensure that all fibers follow the same path between the electronics module 2 and transducer 1 and so experience similar environmental effects and in particular are subject to the same bending and microbending forces.

Figure 6:
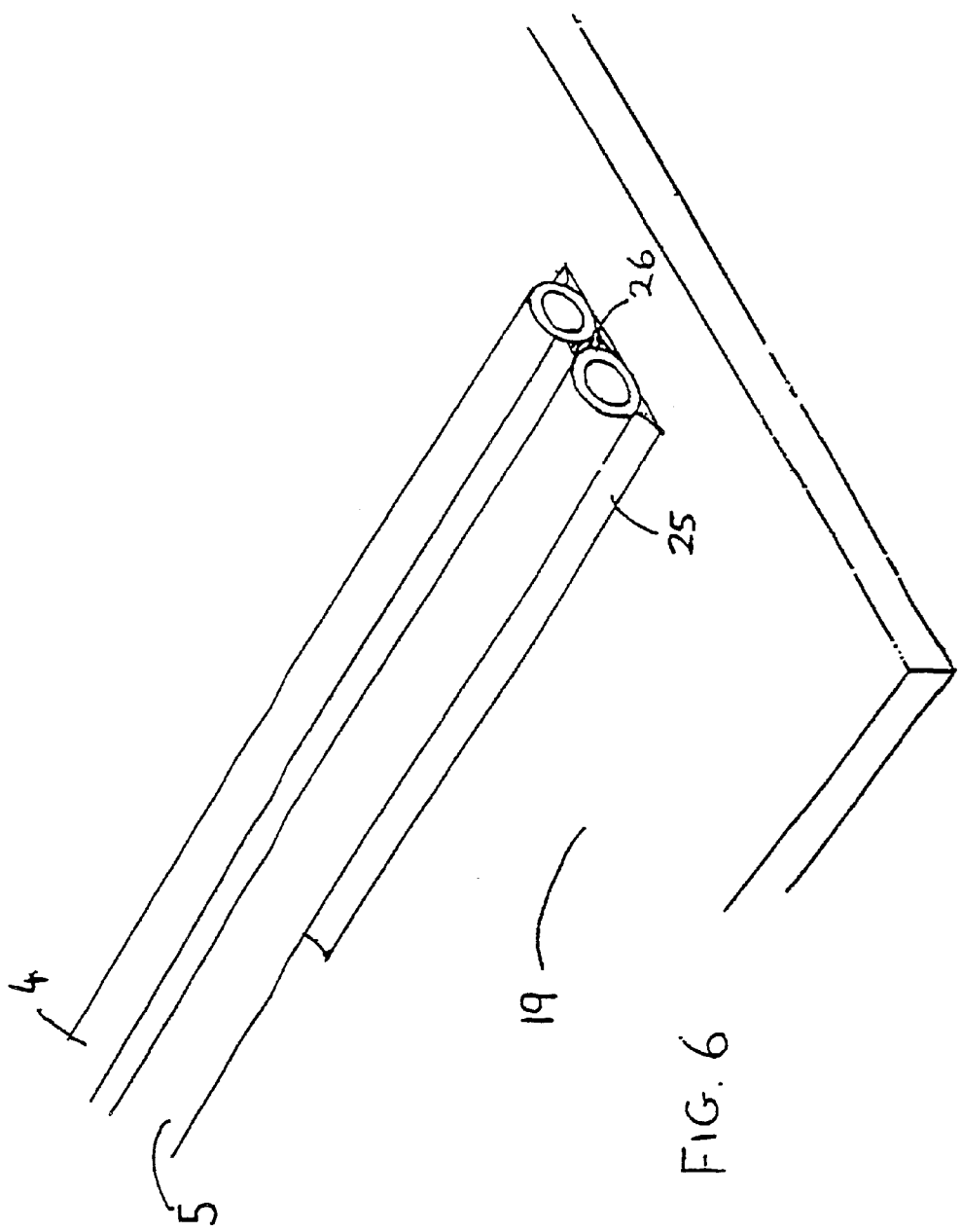
FIG. 6 is a pictorial view of the proximal end of the optical fibers.

FIG. 6 illustrates in greater detail the termination of the fiber sets at the transducer. The fibers constituting the measurement channel 4, 5 are joined longitudinally at the end proximal to the transducer using epoxy glue 26. The proximal end faces of the fibers are then ground and polished flush with each other to provide an efficient optical coupling between the fibers and a light-reflective surface 35 of a measurement channel shutter-reflector structure 24 that is attached to the underside of a pressure plate 23 (FIG. 4). The joined fibers are glued into position on the substrate plate 19 (FIG. 6) using an ultraviolet curing glue 25. The reference channel fibers 6, 7 are assembled following a similar procedure.

Guide rails 22 mounted on the substrate plate 19 (FIG. 3) provide a convenient aid to the positioning of the fiber sets so that the proximal end faces of the fibers will be located a prescribed distance from the reflective surface 35 of the shutter-reflector structure 24 which, as noted, is attached to the pressure plate 23, in the case of the measurement channel. Another shutter-reflector structure 20 with reflective surface 36 is attached to the substrate plate 19 (FIG. 4) in the case of the reference channel optical fiberset 6, 7. The guide rails 22 also aid the positioning of the fibers so that the optical axis of the set of fibers is roughly perpendicular to the respective reflective surfaces.

Figure 3:
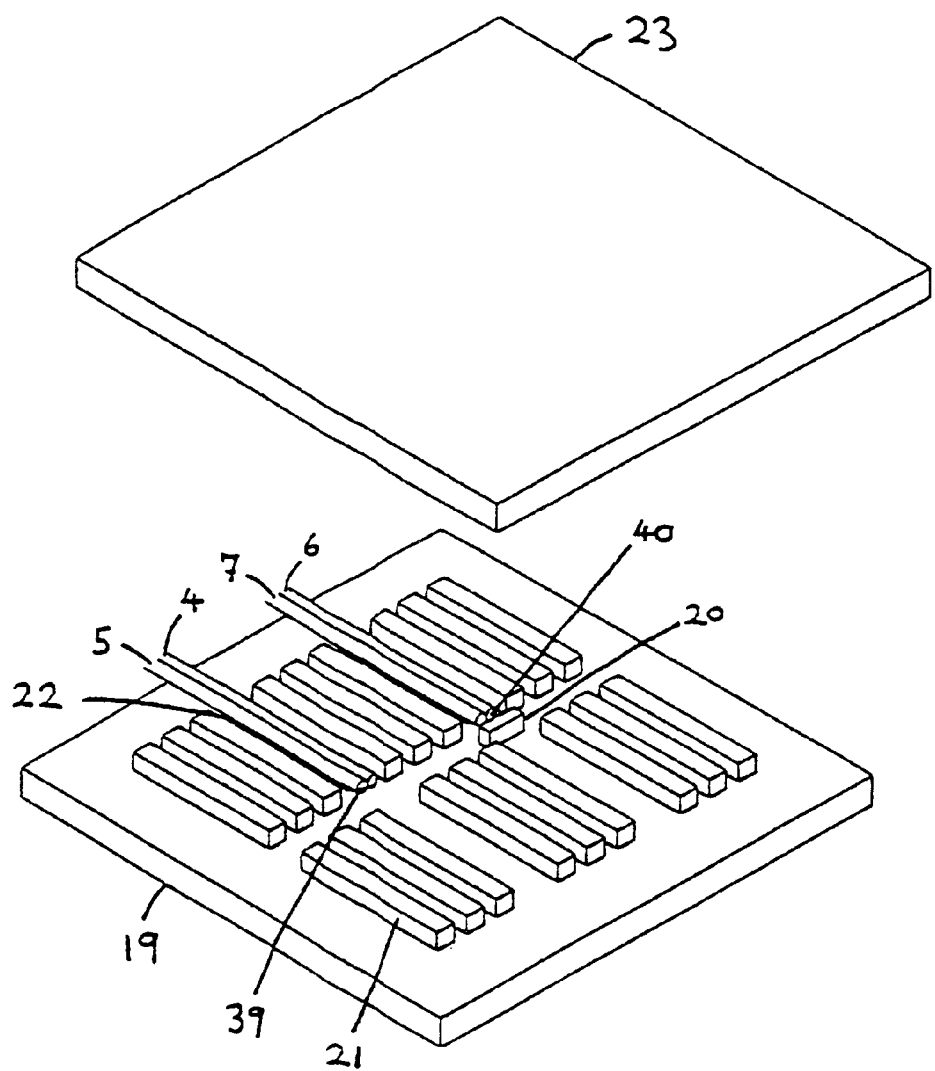
FIG. 3 is a pictorial representation of the substrate and pressure plates, respectively, of the preferred embodiment.
Figure 5:
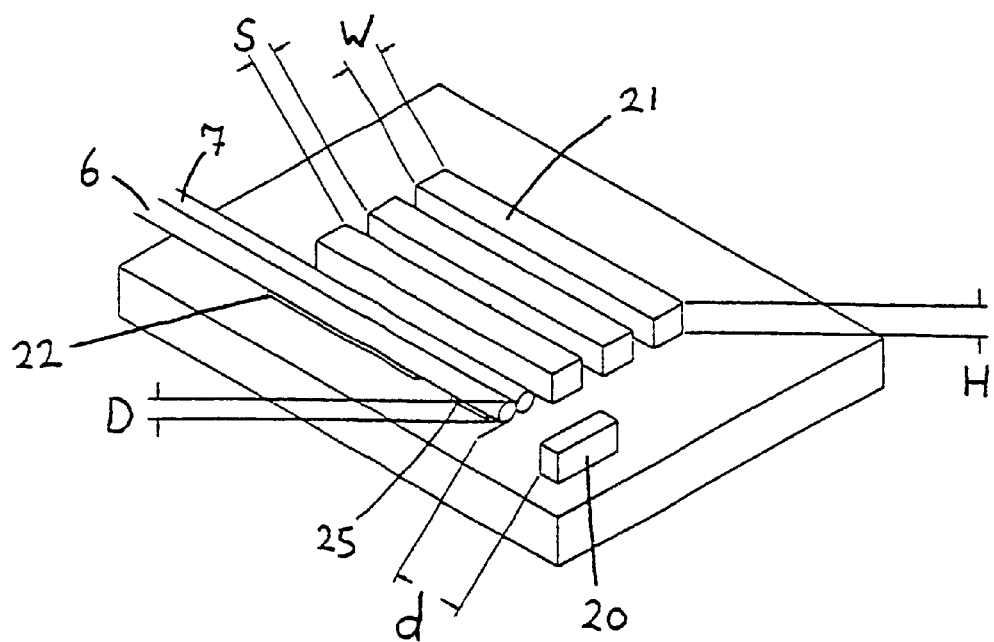
FIG. 5 is an enlarged fragmented pictorial view of the substrate plate of the preferred embodiment.

FIGS. 3, 4, 5 show the substrate 19 and pressure plates 23 of a pressure transducer in accordance with the preferred embodiment of the invention and in particular illustrates in greater detail the positioning guide-rails 22, the deformable polymer structure 21 (FIG. 5) and the shutter-reflector structures 20, 24. Identical alumina plates (96% Koyrea) are used for both the substrate 19 and pressure plates 23 of the device. While alumina plates are used in the preferred embodiment of the invention a wide range of alternative plate materials may also be used depending upon the application. The deformable polymer structure 21 may be formed from a material such as silicone rubber, polyurethane rubber, and linear polybutadiene. In the preferred embodiment illustrated, RTV silastic silicon rubber 9161, having a weight of catalyst to total weight ratio in the region of 2–6%, is used to form the deformable polymer structure 21.

In the preferred embodiment of the invention RTV silastic rubber is also used to form the guide-rail structures 22. These structures might also be formed from a wide range of polymer or ceramic dielectric materials.

In the preferred embodiment of the invention RTV silastic rubber is also used to form the shutter-reflector structures 20, 24. Metal elements with high reflection coefficients may be used as the shutter-reflector structure. Alternatively, metal coatings in conjunction with polymer or other non-metallic bodies might also be used for such structures. However, a particular advantageous consequence of using RTV silastic rubber to form the shutter-reflector is that it can be formed with smooth flat surfaces which act as good reflectors for the wavelengths available in common visible and infrared (IR) emitting diodes. In addition, the material does not tarnish and is substantially opaque to both visible and IR radiation. Thus, it is possible to manufacture the transducer according to the invention from all non-metal materials.

A number of techniques such as photolithographic printing, molding, and thick-film screen-printing may be used to form the polymer structures directly onto the alumina plates. This range of techniques offers the ability to form the polymer materials into a wide range of planar geometrical patterns of preselectable thickness.

The pattern of the deformable polymer structure 21 is chosen so as to produce the optimum deformation characteristics for the application. The planar pattern can be selected from a wide range including striped, rectangular, circular or crossed shapes. Important deformable polymer structure parameters to control relate to the cross-sections of the individual projections of the structure, the spacing between individual neighboring projections, and contact area between the plates and the top and bottom faces of the projections.

In the present embodiment, the optimum span to base width ratio, (S/W), for individual projection cross-sections is within a range from 0.4 to a maximum of 10 (See FIG. 5). At ratios greater than 10, excessive deformations will be encountered in the structure which will cause increased non-linearity in the relationship between the compressive stress in the body and the deformation of the body, and, a reduced working range for the device. An S/W ratio of less than 0.4, on the other hand, may cause contact between adjacent individual projections within the deformable polymer structure 21.

The ratio of the base width to the height of the individual projections constituting the deformable polymer structure 21, W/H, can vary from a value of 0.8 to 10. A value of 0.8 would lead to a structure which would have relatively low resistance to shear loading. For values of W/H greater than do the sensitivity of the transducer would be so low as to make the device impractical as a simple pressure transducer. In addition, this would lead to increased hysteresis in the relationship between applied pressure and the deformation.

In order to maintain a linear response, the full load deformation is limited to a value of 20% of the deformable structure height, H. This translates to a practical limit of 8 for the ratio $A_p/A_R$ where $A_p$ is the total area of the pressure plate and $A_R$ is the total contact area of the deformable polymer structure 21 with the substrate plate 19. $A_R$ is the product of N (number of deformable bodies) and W (base width of cross section) and L (length of deformable body).

The selection of the diameter of the optical fiber and the heights of the deformable polymer structure 21, and the shutter-reflectors 20, 24 are important in determining the transducer sensitivity, linearity, and dynamic range, as is the distance, d, between the particular channel shutter-reflector and the corresponding optical fiber set proximal faces 39, 40 measured in the plane of the plates (FIG. 3).

The ratio of the height of the deformable polymer structure 21, H, to the fiber diameter, D, should be within a range defined by:

$$1.25 \leq \frac{H}{D} \leq 4$$

for a transducer according to the preferred embodiment illustrated in FIG. 5. If this ratio is greater than 4, then the transducer will saturate under high loads. The lower limit represents a practical limit set by the necessity to ensure that the pressure plate 23 does not come to bear on the fiber under high load conditions.

The height of the measurement channel shutter-reflector 24 (that is, from the underside of the plate 23) is selected so that, under zero load conditions of the transducer, between 10% and 80% of the area of the geometrical projections of the emitting and detecting faces 39, 40 of the measurement channel optical fibers intersect or overlap the reflecting surface 35 of that reflector 24.

The corresponding overlap for the reference channel is usefully set to approximately 50% although the exact value is not critical to the satisfactory operation of the device.

In the preferred embodiment of the invention, the angle between the emitter fibers 4, 6 and the detector fibers 5, 7 at the proximal ends 39, 40 of each .fiber set is approximately 0°. The maximum sensitivity occurs for a spacing, d, between the shutter-reflector reflecting face and the proximal end faces of the fiber sets given by:

$$d = \frac{D}{2 \, \text{Tan}(\text{Arcsin } NA)},$$

where D is the fiber diameter and NA is the fiber numerical aperture. Good transducer performance is possible where this distance is within the range 1.25 to 1.75 d for both the measurement and the reference channel. This corresponds to a region where the light intensity of the reflected beam is less sensitively dependent on the exact spacing between the fiber ends and the reflective surface while at the same time a high rate of change of optical coupling occurs for transverse movement of the shutter-reflector reflective surface 35 into the measurement channel light beam.

The guide-rails 22 formed on the substrate plate 19 greatly facilitate initial course placement of the fibers. A degree of initial preset and trim is possible by monitoring the photodetector 8, 13 output as the optical fibers are positioned in the assembly process.

Figure 7:
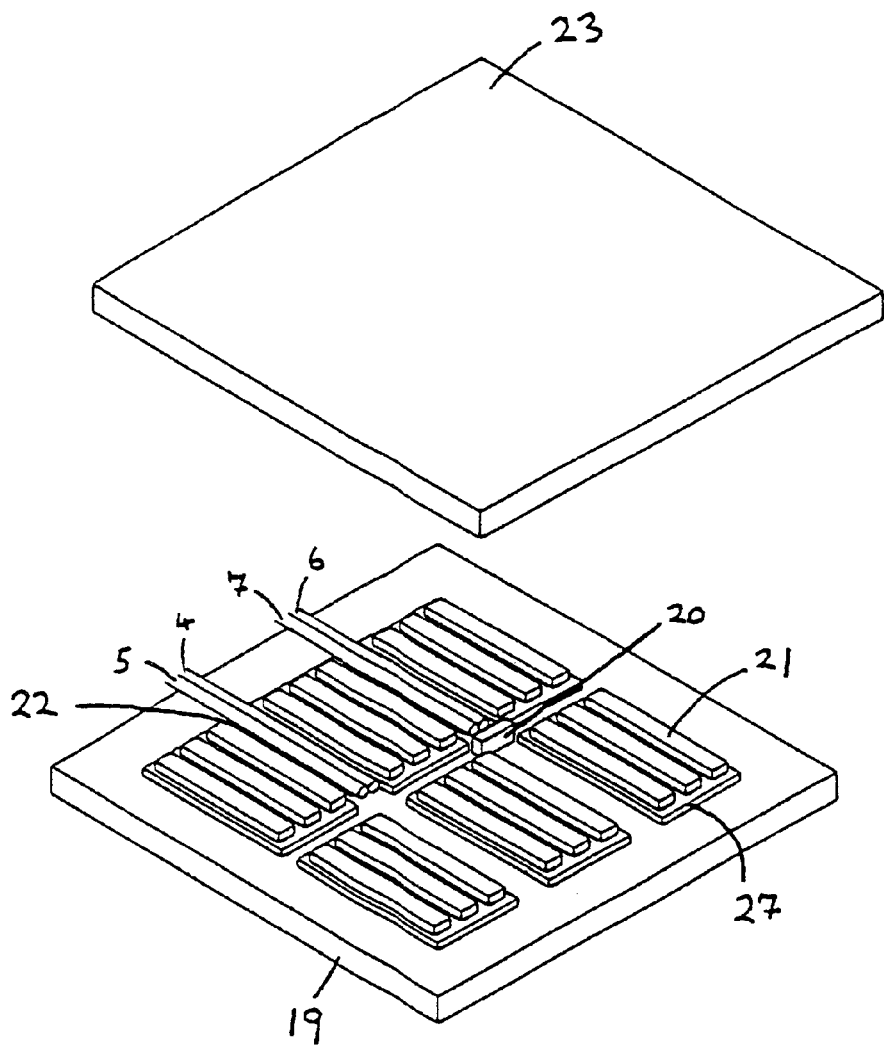
FIG. 7 is a pictorial representation of the substrate and pressure plates of the second preferred embodiment.
Figure 8:
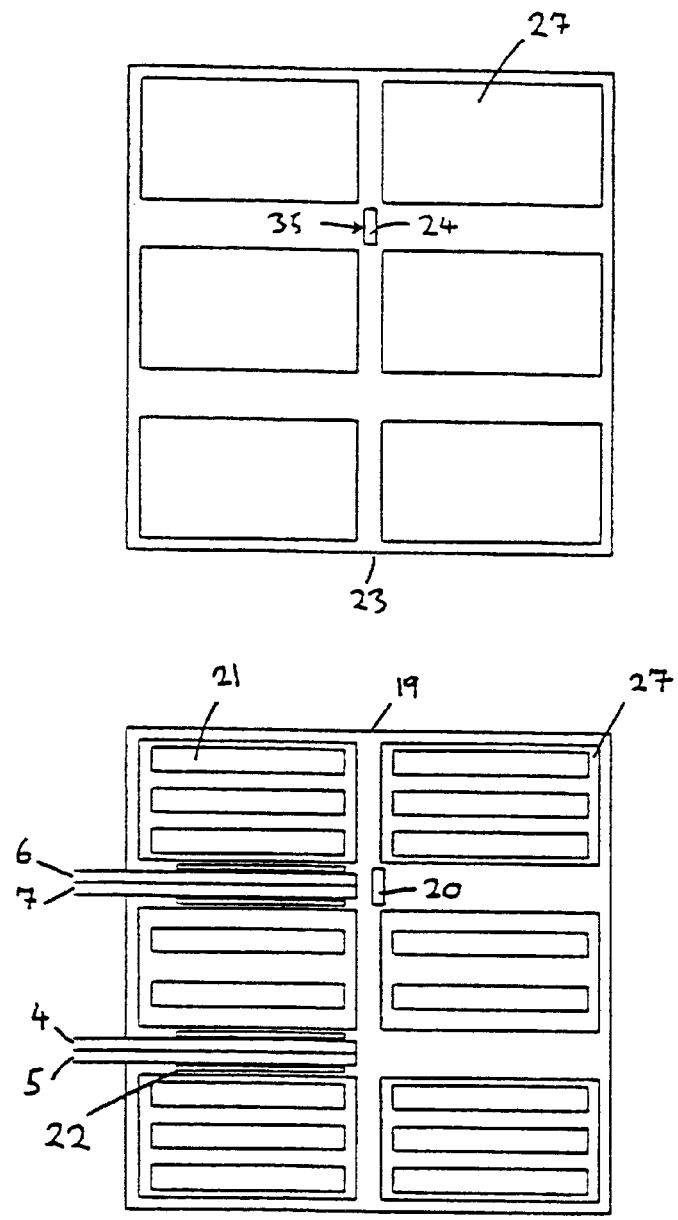
FIG. 8 is a plan view of the substrate and pressure plates of the second preferred embodiment.
Figure 9A:
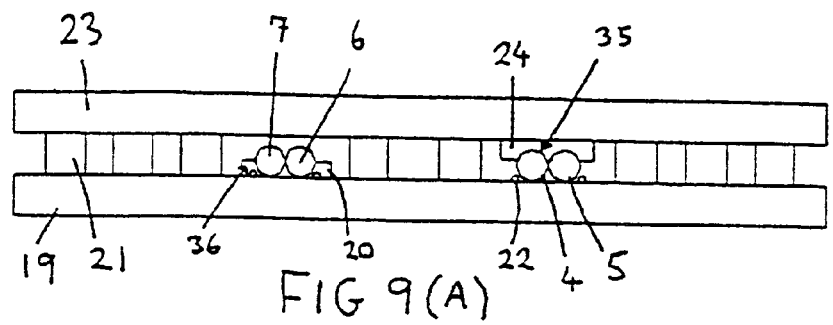
FIGS. 9(A), 9(B) and 9(C) respectively depict an end view and cross sectional views of the preferred embodiment.
Figure 9B:
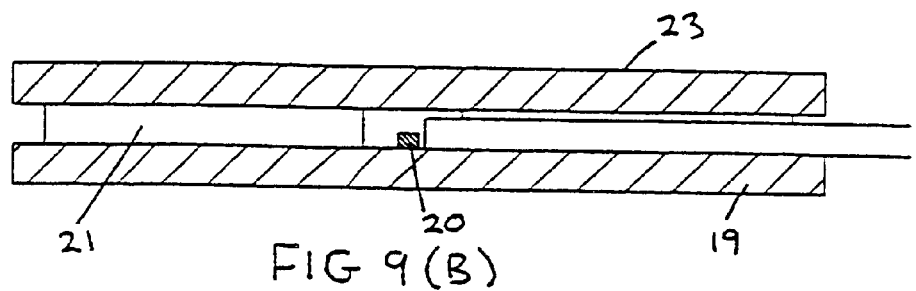
Figure 9C:
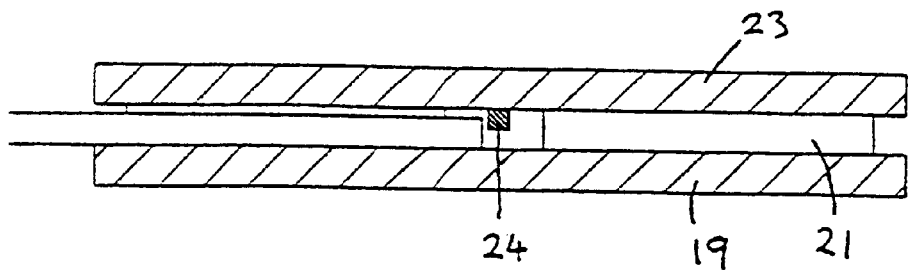
Figure 10:
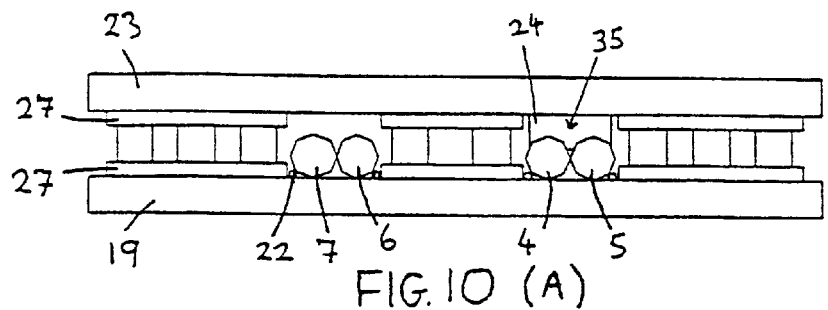
FIGS. 10(A), 10(B) and 10(C) respectively depict an end view and cross sectional views of the second preferred embodiment.
Figure 10:
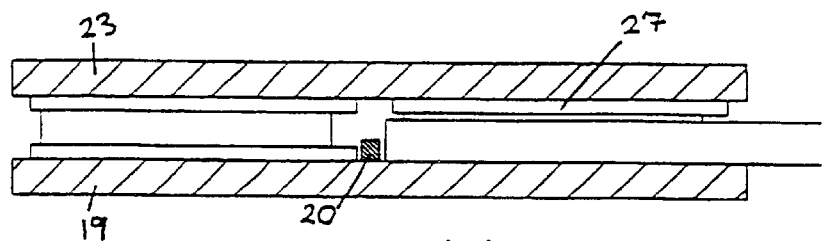
Figure 10:
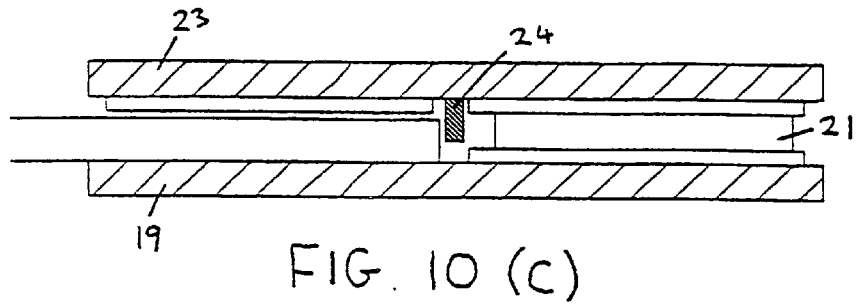

A second preferred embodiment is shown in FIGS. 7, 8, and 10 where substantially non-deformable pads 27 are used in conjunction with deformable polymer structures 21 to manufacture a transducer according to the invention. An advantageous way of manufacturing the substantially non-deformable pads 27 involves using RTV silastic silicon rubber 9161 in the form of a largely continuous layer where the thickness of the layer is less than 5% the layer width and less than 5% of the layer length. This latter condition ensures that the deformation of the pad for the range of pressures of interest in this invention is negligible.

This preferred embodiment is particularly advantageous where reduced height deformable polymer structures 21 are to be used. A practical range for such structures is defined within the limits:

$$0.25 \leq \frac{H}{D} \leq 1.5.$$

This may occur, for instance, where it is desirable for reasons such as economics of manufacture, to have deformable polymer structures 21 with heights similar to or significantly less than the fiber diameter. In this embodiment, substantially non-deformable polymer pads 27 are arranged on each substrate directly above and underneath the deformable polymer structures 21. The pads are in effect spacers designed to increase the spacing between the plates to a value sufficient to allow accommodation of the fibers between the plates and also allow deformation of the deformable polymer structures 21 which is unrestricted by the fibers.

The criterion used in relation to the dimensions of the deformable polymer structure 21 and the shutter-reflectors 20, 24, and, the distance between the shutter-reflectors 20, 24 and the proximal end faces 39, 40 of the optical fiber sets, for the first preferred embodiment, are equally applicable in the case of the second preferred embodiment and will not be detailed further here.

Figure 11:
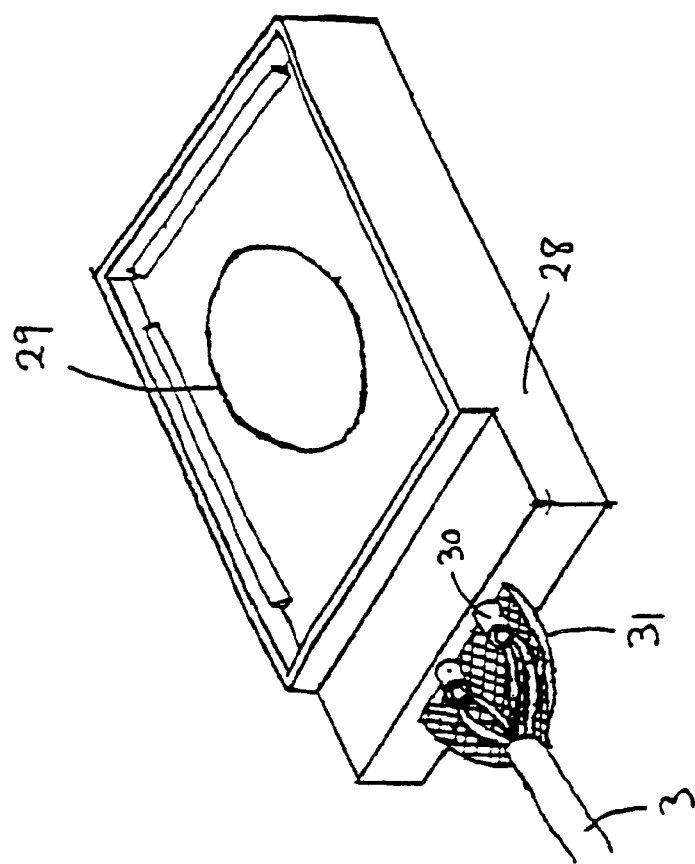
FIG. 11 is a pictorial view of the packaged transducer.
Figure 12A:
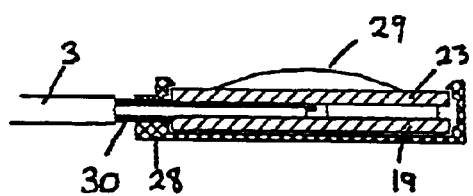
FIGS. 12(A) and 12(B) respectively depict sectional views of the packaged transducer.
Figure 12B:
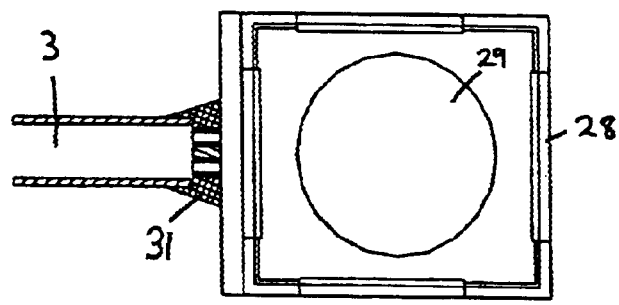

FIGS. 11, 12 illustrate one way of packaging the transducer 1. The package 28 should be made from some non-metallic material such as HDPE, Nylon or Teflon. The profile of the package 28 must be at least as low as the complete transducer under maximum compression. A polymer cap 29 attached to the outer surface of the pressure plate 23 ensures that this requirement is satisfied. In addition, the cap 29 may help to reduce shear force interference and to better translate the applied pressure to the transducer 1.

The measurement channel optical fiber set is passed through a flexible sleeve 30 which is located in the transducer package wall. The flexible sleeve 30 will be made of the usual materials known for use in fiber optic cabling. The sleeve's internal diameter is slightly greater than the combined diameters of the fibers in the set so that they readily fit within it. Epoxy is then drawn into the sleeve to fill the space between the fibers and the internal wall of the sleeve 30. This sleeve provides a flexible strain-relieving conduit for fiber passage through the transducer package wall. A similar arrangement may be used with the reference channel optical fiber set. A molded buffer 31 provides further protection and stress relief for the joint between the fiber cable containing both sets of fibers and the transducer package 28.

It is widely accepted that fiber optic transducers based upon intensity modulation principles are particularly susceptible to interference effects due to source and detector temperature fluctuations, aging effects, and bending and environmental effects along the path of the fibers, as well as variations in the reflectivity of reflecting surfaces. Such effects can produce intensity variations which are indistinguishable from the intensity modulation produced by the parameter of interest and so introduce significant uncertainty in the measurement process.

In accordance with the invention, the transducer 1 includes a second set of optical fibers which form a reference channel and which are located within a plastic jacket 3 which links the transducers and the electronics module 2 and which also contains the measurement channel optical fibers. This sleeve is coaxial with the combined sets of optical fibers. The shutter-reflector attached to the substrate plate 19 with a reflecting surface 36 and arranged as described above has a fixed position with respect to the proximal end faces 40 of the reference channel fiber set. It therefore reflects a predetermined proportion of the light emitted by the reference emitter fiber 6 into the reference detector fiber 7. The reference light beam is therefore not modulated by pressure applied to the plates. However, it will be subject to the interference effects listed above. Since the fibers of the reference channel are arranged to follow largely the same path between the electronics module 2 and the transducer 1 as the measurement channel fibers, the intensity of the reference channel light signal may be used to neutralize to a significant extent the effects of such interference effects. Furthermore, significant immunity to electromagnetic noise interference and electrical drift within the electronic processing circuitry is ensured through the use of non-DC signals.

Several factors inherent in the manufacturing of the transducer cause an uncertainty or inaccuracy in the relationship between the applied pressure and the measured pressure. These factors include uncertainties in the geometry of the reflecting surface, uncertainties in the relative positions of the fibers with respect to the reflecting surfaces and uncertainties in the fiber connections and terminations. Any such inaccuracy associated with the measurement signal can be compensated for by appropriately calibrating each transducer. In particular, this can be accomplished by placing the transducer 1 in a simple jig which contains an adjustable clamp which can be brought to bear on the pressure plate of the transducer in order to apply a known pressure to the transducer 1.

In use, the transducer 1 may be inserted between a tourniquet cuff 18 and a limb or tissue (FIG. 1). The pressure transducer 1 is designed to be sufficiently thin that it does not displace substantially the tissue from its normal location in relation to the tourniquet cuff 18. The pressure applied by the cuff 18 to the tissue may be determined using the transducer 1 in conjunction with appropriate electronics circuitry. When pressure is applied to the transducer 1, the deformation of the deformable polymer structure 21 will result in a change in the degree of projection of the measurement channel shutter-reflector 24 into the measurement channel light beam. This will change the coupling of light between the measurement channel emitter fiber 4 and detector fiber 5 and thereby modulate the measurement channel light beam.

With reference to FIGS. 1 and 2(A), a measurement photodetector 13 located at the distal end of the measurement channel detector fiber 5 produces an electrical signal which is representative of the intensity modulation of the measurement channel light beam. This is fed to an amplifier 14 which in turn is connected to an analogue-to-digital converter 15 before being passed in digital form to the processor 16.

The intensity reference signal available from the reference channel photodetector 8 is processed in a similar way to the measurement channel signal. The signals may be digitally processed by the processor 16 to produce an output reading, which is compensated for non-measurand related intensity variations. One simple approach would involve obtaining ratiometric output, which is representative of the applied pressure. However, a simple alternative compensation technique would involve using the intensity reference signal to provide a feedback control signal to the LED pulse driver circuit 12 in order to maintain the intensity of the beam in the reference channel at a constant set-point level. Both compensation techniques are well known and will not be described further here.

The transducer 1 can thus provide the physician with a non-electrical means of determining the pressure applied by the cuff 18 at a predetermined location under the cuff 18.

Figure 13:
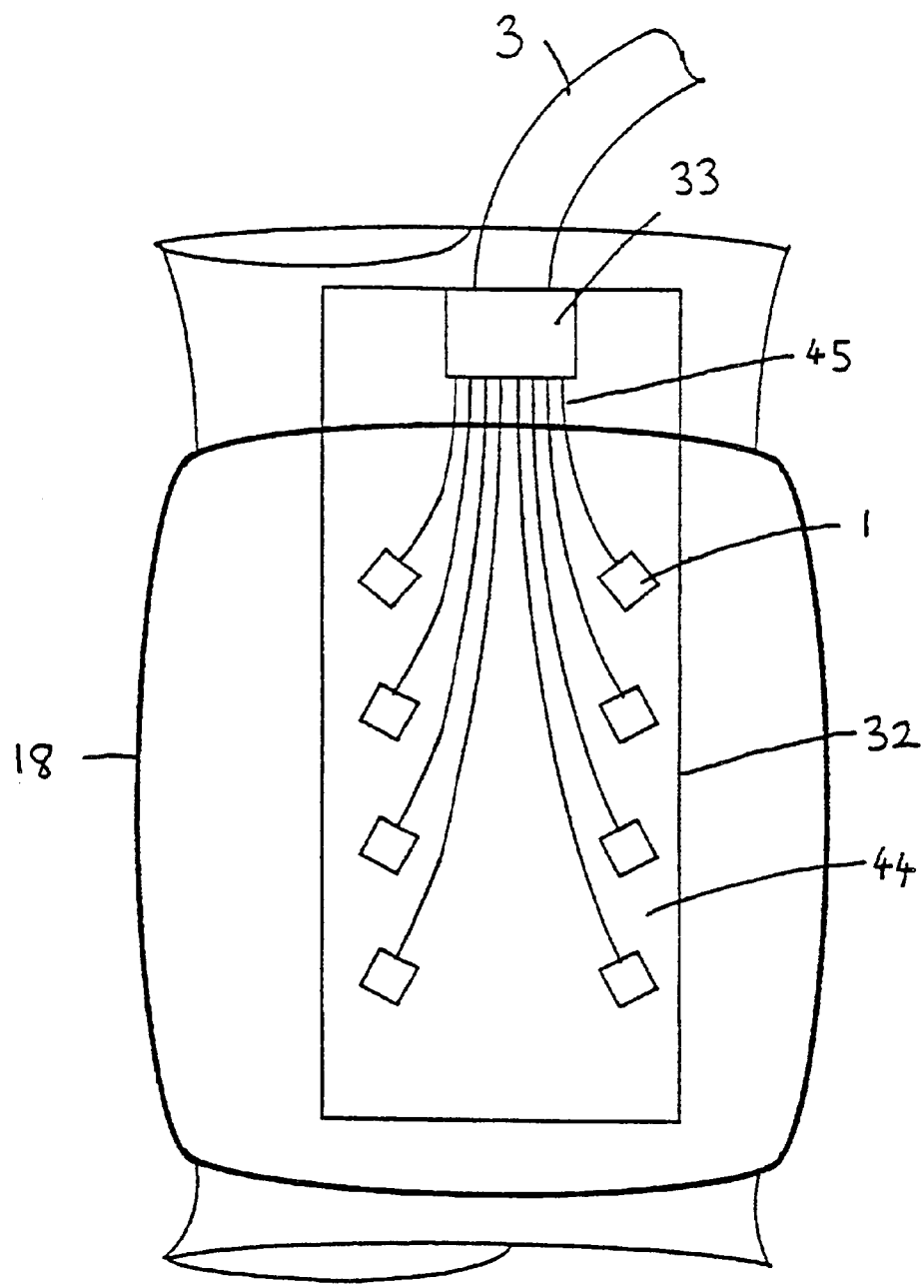
FIG. 13 depicts the multi-transducer array of transducers made in accordance with the present invention.

Due to ability to produce transducers of minimal thickness and width a number of transducers may be attached to a flexible carder layer 32 such as Mylar (Dupont trademark) sheet to form an array. FIG. 13 demonstrates a 2×4 array 44 which may be placed under a tourniquet cuff 18 in order to provide a measurement of the pressure distribution profile applied to an underlying limb or organ by the cuff 18. The carrier layer provides a landing platform which facilitates anchoring of the plastic jacket 3 using an anchor strap 33. The layer 32 also carries the various sets of optical fibers and allows convenient fan-out of the individual fiber optic sets.

The four fibers constituting the measurement channel and reference channel optical fiber sets for a given transducer of the array 44 are contained within flexible polymer sleeves 45 which are attached using an epoxy glue to the carrier layer 32. Care is taken with the arrangement of the individual transducers 1 to ensure that any bending in the fibers in order to allow all transducers be accessed with appropriate sets of fibers does not contravene the manufacturer's recommended long term minimum bend radius for the fibers concerned. For convenience, the entire array 44 may be attached to the inner surface of the cuff 18 using double-sided adhesive tape or other simple joining means. The driver circuitry and signal processing circuitry is replicated in the control module for each transducer of the array.

While there have been described what are presently believed to be the preferred embodiments of the invention, it will be apparent to one skilled in the art that numerous changes can be made in the structure, materials, proportions and conditions set forth in the foregoing embodiments without departing from the invention as described herein and as defined in the appended claims. For instance, while the preferred embodiments described above use modulation of a reflected light beam to infer the pressure applied to the transducer, clearly, modulation of a transmitted beam could also be used. Also, a fiber 'T' coupler could be used to provide two beams from the single source LED for the emitter fibers of both the measurement and reference channels. More particularly, a fiber optic beam splitter with demountable connectors could be used for this purpose. Similarly, demountable connectors could be used for connecting the detector fibers to the photodetectors. Furthermore, it is conceivable that the transducer with connecting fibers and the necessary light source and detectors could be assembled at low cost as a single disposable unit.

What is claimed is:

1. A planar transducer for measuring biomedical pressures which comprises:

a substrate plate and an opposing pressure plate;

a measurement channel optical fiber set with proximal and distal ends, said proximal end being attached to said substrate plate, said distal end being connectable remotely to an electronics module;

a reference channel optical fiber set with proximal and distal ends, said proximal end being attached to said substrate plate, said distal end being connectable remotely to an electronics module;

a deformable polymer structure disposed between the substrate and pressure plates;

a measurement channel shutter-reflector structure attached to said pressure plate, said shutter-reflector having a reflective surface that faces the measurement channel optical fiber set proximal end;

a reference channel shutter-reflector structure attached to said substrate plate, said shutter-reflector having a reflective surface that faces the reference channel optical fiber set proximal end; and the transducer being configured so that when said plates are pressed toward one another the measurement channel shutter-reflector structure modulates a light beam that is transmitted in the measurement channel optical fiber set in correlation with a variation in the deformation of the deformable polymer structure.

2. The transducer of claim 1 wherein the measurement fiber set and the reference fiber set each comprises an emitter and a detector fiber.

3. The transducer of claim 1 wherein the deformable polymer structure comprises a plurality of projections.

4. The transducer of claim 1 wherein the ratio of the height of the deformable polymer structure to the optical fiber diameter is between 1.25 and 4.

5. The transducer of claim 1 wherein the measurement channel shutter-reflector is sized such that, under zero load conditions of the transducer, between 10% and 80% of the area of the geometrical projections of the proximal ends of the measurement channel fiber optic set overlaps the reflecting surface of the measurement channel shutter-reflector.

6. The transducer of claim 1 wherein said transducer has a dimensional extent in a direction normal to the plates which is reduced relative to the dimensional extent of said transducer in the plane of the plates.

7. The transducer of claim 1 further comprising an optical fiber positioning means comprising polymer guide-rails attached to the substrate plate.

8. The transducer of claim 1 further comprising calibrating means for calibrating the transducer in terms of known values of pressure associated with the measurement channel wherein the calibrating means includes clamps for clamping the transducer, one of the clamps being movable relative to the other in order to impose predetermined pressure to the pressure plate.

9. The transducer of claim 1 wherein the transducer is one of an array of such transducers mounted on a flexible layer.

10. The transducer of claim 9 wherein the dimensions of the transducers and flexible layer are selected so that the array may be interposed between a tourniquet cuff and a limb to conform to the limb and not substantially displacing the limb surface from the cuff surface.

11. The transducer of claim 1 further comprising
   a set of substantially non-deformable pads formed on each plate; wherein the deformable polymer structure is disposed between said non-deformable pads.

12. The transducer of claim 11 wherein measurement fiber set and the reference fiber set of claim 11 each comprises an emitter and a detector fiber.

13. The transducer of claim 11 wherein the deformable polymer structure comprises a plurality of projections.

14. The transducer of claim 11 wherein the ratio of the height of the deformable polymer structure to the optical fiber diameter is between 0.25 and 1.5.

15. The transducer of claim 11 wherein the substantially non-deformable pads comprise a continuous or semi-continuous polymer layer.

16. The transducer of claim 15 wherein polymer layer has a thickness less than 5% the layer width and less than 5% of the layer length.

17. The transducer of claim 1 wherein the reference channel shutter-reflector is sized such that, under zero load conditions of the transducer, between 10% and 80% of the area of the geometrical projections of the proximal ends of the reference channel fiber optic set overlaps the reflecting surface of the reference channel shutter-reflector.

18. The transducer of claim 1 including an electronics module to which the distal ends of the reference channel optical fiber set and of the measurement channel optical fiber set are connected.

* * * * *